United States Patent [19]
Weber

[11] Patent Number: 5,319,867
[45] Date of Patent: * Jun. 14, 1994

[54] ELECTRICALLY CONDUCTIVE SHOE INSOLE

[75] Inventor: Fredric J. Weber, Waco, Tex.

[73] Assignee: Spenco Medical Corporation, Waco, Tex.

[*] Notice: The portion of the term of this patent subsequent to Aug. 10, 2010 has been disclaimed.

[21] Appl. No.: 58,020

[22] Filed: May 5, 1993

Related U.S. Application Data

[63] Continuation of Ser. No. 807,036, Dec. 12, 1991, Pat. No. 5,233,769.

[51] Int. Cl.$^5$ .................. A43B 13/18; A61N 1/14
[52] U.S. Cl. ................................. 36/44; 36/43; 361/224
[58] Field of Search ............... 36/43, 44, 113; 361/223, 224

[56] References Cited

U.S. PATENT DOCUMENTS

| | | |
|---|---|---|
| 46,234 | 2/1865 | Hall . |
| 495,782 | 4/1893 | Carnes . |
| 2,261,072 | 10/1941 | Monahan . |
| 2,641,068 | 6/1953 | Thompson . |
| 2,671,185 | 3/1954 | Bloom . |
| 2,710,366 | 6/1955 | Stern, Jr. et al. . |
| 2,879,452 | 3/1959 | Page . |
| 3,007,083 | 10/1961 | MacQuaid, Jr. . |
| 3,449,844 | 6/1969 | Spence . |
| 3,852,897 | 12/1974 | Bridge et al. ................ 36/44 |
| 4,015,347 | 4/1977 | Morishita et al. .............. 36/44 |
| 4,150,418 | 4/1979 | Berbeco ........................ 361/224 |
| 4,223,458 | 9/1980 | Kihara ............................ 36/44 |
| 4,249,226 | 2/1981 | Westberg et al. ............ 361/223 |
| 4,642,912 | 2/1987 | Wildman et al. ............... 36/44 |
| 4,703,754 | 11/1987 | Ibbott ........................... 128/383 |
| 4,785,371 | 11/1988 | Edwards ....................... 361/224 |
| 4,864,740 | 9/1989 | Oakley ........................... 36/44 |
| 4,925,724 | 5/1990 | Ogden ........................... 428/137 |
| 4,926,570 | 5/1990 | Fohst ............................. 36/43 |
| 5,233,769 | 8/1993 | Weber ............................ 36/44 |

FOREIGN PATENT DOCUMENTS

| | | | |
|---|---|---|---|
| 5232744 | 9/1975 | Japan ............................. 36/44 |
| 62-298303 | 12/1987 | Japan ............................. 36/44 |

Primary Examiner—Steven N. Meyers
Attorney, Agent, or Firm—Thomas J. Connelly

[57] ABSTRACT

An electrically conductive shoe insole is disclosed for cushioning a user's foot and for transferring electrical charges from the wearer's foot to a conductive shoe. The shoe insole includes a cushioned layer, which contains an electrically conductive material, and a fabric, which is bonded to the top surface of the cushioned layer by a nonconductive adhesive. The fabric contains a noncorrosive electrically conductive fiber interwoven therein. The adhesive is applied such that the electrically conductive fibers in the fabric contact the cushioned layer. This allows transfer of electrical charges from the fabric to the cushioned layer.

16 Claims, 3 Drawing Sheets

ELECTRICALLY CONDUCTIVE SHOE INSOLE

This is a continuation application of copending application Ser. No. 07/807,036, filed on Dec. 12, 1991 now U.S. Pat. No. 5,233,769.

FIELD OF THE INVENTION

This invention relates to an electrically conductive shoe insole which uses a nonconductive adhesive.

BACKGROUND OF THE INVENTION

Electrically conductive shoe insoles are used to keep static electrical charges from building up on a worker's body. Friction can develop between a person's hands and feet when in contact with other surfaces, and this can cause an accumulation of electrostatic charges as the person moves about. These electrostatic charges can pose a serious threat of injury if the air contains combustible gases or flammable liquids, as in a munitions factory. The build up of electrostatic charges on the body can cause a spark when a worker touches a grounded metal object. Depending on the conditions, the spark may cause the airborne combustibles to explode.

To prevent explosions, workers in combustible-laden work areas normally wear electrically conductive shoes. These shoes keep electrostatic charges from accumulating by providing a conductive path of relatively low electrical resistance from a worker's foot to the floor. Electrically conductive insoles must be used in the electrically conductive shoes to maintain the conductive path. This allows the electrical charges to be transferred from the user's foot to the conductive shoe. Patents which describe various types of such shoe insoles include: U.S. Pat. Nos. 4,150,418 issued to Berbeco; 4,642,912 issued to Wildman et al. and 4,926,570 issued to Fohst; as well as Japanese patents 88-039658/06 issued to Kokoku and 52-32744 issued to Sato.

It has been discovered that conventional electrically conductive insoles progressively lose their ability to conduct electrical charges through a process known as degradation. Such shoe insoles typically consist of a base layer rendered electrically conductive and an upper layer of conductive fabric laminated to the base layer with an electrically conductive adhesive. Degradation is apparently caused by perspiration from the user's foot seeping into the fabric. The perspiration may corrode metallic conductive elements or cause the electrically conductive adhesive to crepe and exude through the fabric. Either effect increases the overall electrical resistance of the shoe insole and lowers its ability to conduct electrical charges.

Degradation of an electrically conductive shoe insole is often subtle but can become lethal. It usually starts slowly, then accelerates rapidly as the electrically conductive adhesive begins to exude through the fabric. If undetected, this degradation may cause a sudden, spark-induced explosion.

Consequently, there is a need for an improved shoe insole which can maintain its electrically conductivity over time and which can resists degradation from human perspiration.

SUMMARY OF THE INVENTION

Briefly, this invention relates to an electrically conductive shoe insole which uses a nonconductive adhesive. The shoe insole includes a cushioned layer for absorbing shock, distributing pressure, and transferring electrical charges to an electrically conductive shoe. The cushioned layer contains an electrically conductive material, such as particles of carbon black, which are uniformly distributed throughout. The shoe insole also includes a woven fabric positioned above the cushioned layer which allows moisture to be transferred away from the wearer's foot. The woven fabric is designed to allow electrical charges, which have built up on or within the wearer's foot, to be transferred to the cushioned layer. The woven fabric is constructed of from about 90-99 percent by weight of synthetic noncellulosic fibers and from about 1-10 percent by weight of a noncorrosive electrically conductive element which is interwoven in the fabric. The woven fabric is laminated to the cushioned layer by an electrically nonconductive adhesive.

The general object of this invention is to provide an electrically conductive shoe insole for transferring electrical charges from a wearer's foot to an electrically conductive shoe. A more specific object of this invention is to provide an electrically conductive shoe insole which uses an electrically nonconductive adhesive between the cushioned layer and the woven fabric.

Another object of this invention is to provide an electrically conductive shoe insole which can absorb shock, distribute pressure, and transport moisture away from the wearer's foot.

Still, another object of this invention is to provide a fabric covered, cushioned, laminated shoe insole using a nonconductive adhesive.

A further object of this invention is to provide an electrically conductive shoe insole having a cushioned layer adhesively bonded to a woven fabric, such that the adhesive is inhibited from exuding through the woven fabric.

Still further, an object of this invention is to provide a low-cost, electrically conductive shoe insole which is less likely to degrade over time compared to current electrically conductive shoe insoles.

Other objects and advantages of the present invention will become more apparent to those skilled in the art in view of the following description and the accompanying drawings.

DETAILED DESCRIPTION OF THE PREFERRED EMBODIMENT

Figure 1:
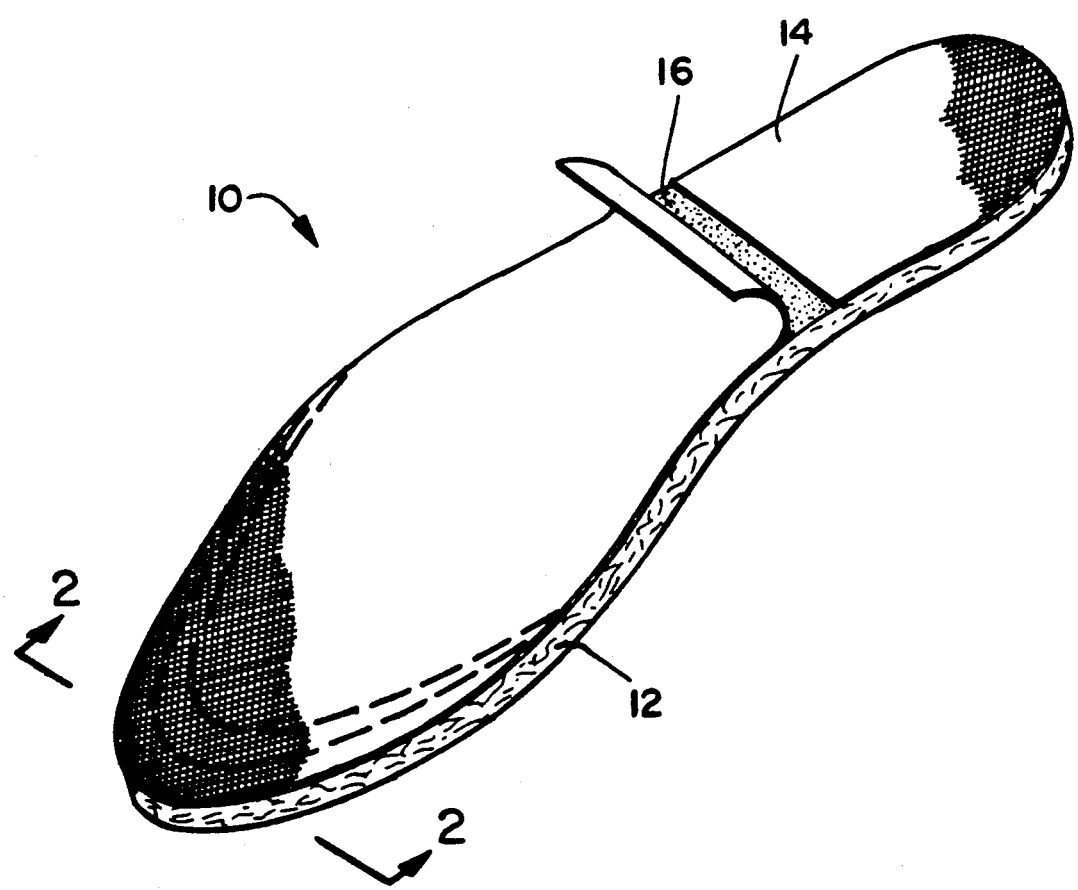
FIG. 1 is a top perspective view of an embodiment of the electrically conductive shoe insole.

Referring to FIG. 1, an electrically conductive shoe insole 10 is shown which includes a cushioned layer 12 and a woven fabric 14 positioned thereabove. The cushioned layer 12 is capable of absorbing shock, distributing pressure, and transferring electrical charges, which may build up in or on the wearer's foot, to a surrounding conductive shoe. The woven fabric 14 is laminated to the cushioned layer 12 by an electrically nonconductive adhesive 16. The woven fabric 14 and the nonconductive adhesive 16 cooperate to inhibit the nonconductive adhesive 16 from exuding through the fabric 14.

Various embodiments of the electrically conductive shoe insole 10 can have an "overall electrical resistance" ranging from about 0 to about 500,000 ohms, preferably, from about 5000 to about 50,000 ohms. The term "overall electrical resistance" refers to the electrical resistance to the flow of electrical current through a sample of material in sheet form at a predetermined voltage potential. One method of determining the resistance of a material is to place a four-inch square sample of the material, which is less than ⅛ of an inch thick, between two horizontally opposed polished aluminum plates. Each plate should have a surface area greater than the area of the sample. The sample is compressed with a force of 5 pounds, and the resistance from the upper plate to the lower plate is measured with an ohm meter, at a 9 volt potential.

The term "fabric" means a textile structure composed of mechanically interlocked fibers or filaments. If the fibers are randomly oriented, the fabric is said to be nonwoven. If the fibers are closely oriented by warp and filler strands at right angles to each other, the fabric is said to be woven. While fabric usually refers to wool, cotton, or synthetic fibers, fabrics can also be made of glass fibers and graphite.

The term "compression set" refers to the resiliency of a material, and more particularly, to the amount of residual deformation or amount of nonrecoverable strain after deflection at room temperature. A method of determining "compression set" of the materials used in the shoe insole is outlined in ASTM D1667-76 entitled, "Standard Specification for Flexible Cellular Materials—Vinyl Chloride Polymers and Copolymers (Closed-Cell Foam)." This test procedure is incorporated by reference and made a part hereof.

The term "electrically conductive", used with respect to resilient rubber or cellular materials, refers to the volume resistivity of a material; the ratio of the electric potential gradient to the current density in a material when the gradient is parallel to the current in the material. A typical method of determining the volume resistivity of resilient materials used in the present invention is outlined in ASTM D991-85 entitled, "Standard Test Method for Rubber Property—Volume Resistivity of Electrically Conductive and Antistatic Products." This test procedure is incorporated by reference and made a part hereof.

A material is considered electrically conductive if it exhibits a volume resistivity of less than 8,050,000 ohm meters. Conversely, a material is considered electrically nonconductive if it exhibits a volume resistivity greater than 8,050,000 ohm meters.

The term "electrically nonconductive", when used with respect to an adhesive compound, refers to the volume resistivity of the compound; the ratio of the electric potential gradient to the current density when the gradient is parallel to the current in a sample of the compound. A typical method for determining the volume resistivity of an adhesive compound used in the present invention is outlined in ASTM D2739-72 entitled, "Standard Test Method for Volume Resistivity of Conductive Adhesives." This test procedure is incorporated by reference and made a part hereof. An adhesive is considered nonconductive if it exhibits a volume resistivity greater than 80,500 ohm meters.

Figure 2:
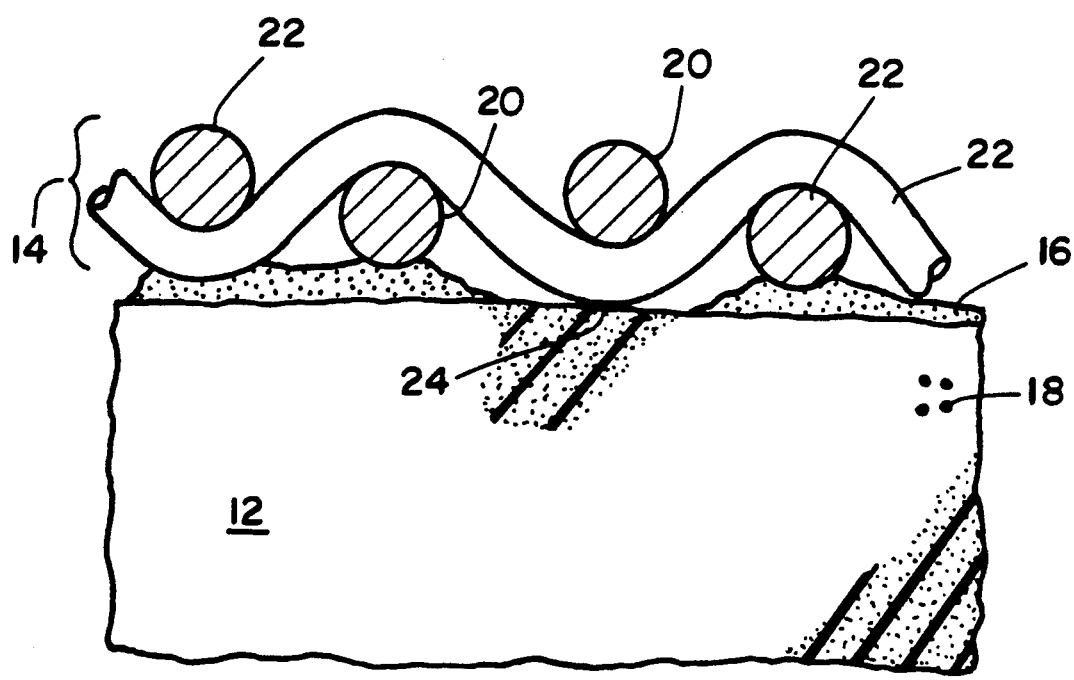
FIG. 2 is an enlarged cross-sectional view of the electrically conductive shoe insole depicted in FIG. 1 and taken along line A—A.

Referring to FIG. 2, the cushioned layer 12 is designed for absorbing shock and distributing pressure. Accordingly, its compression set ranges from about 1 percent to about 50 percent, preferably, from about 5 percent to about 15 percent. The cushioned layer 12 can be made from a foam material, for example a vulcanized foam. The cushioned layer 12 could also be constructed from a closed-cell or from mixed-cell cellular materials. The mixed-cell cellular materials should have a major proportion of closed cells and a minor proportion of open cells. For example, the cushioned layer 12 could be made from one of the following materials: neoprene, butyl rubber, rubbers containing ethylene propylene diene monomers, polyvinyl chloride or polyurethane. For most applications, the cushioned layer 12 should have a thickness which ranges between about 0.01 to about 0.5 inches. Preferably, the thickness ranges between about 0.10 to about 0.15 inches.

An electrically conductive material 18 is contained within the cushioned layer 12 to enable the cushioned layer 12 to transfer electrical charges from the wearer's foot to the surrounding conductive shoe. The electrically conductive material 18 may be particles of carbon black uniformly distributed throughout the cushioned layer 12. Due to the presence of the electrically conductive material 18, the volume resistivity of the cushioned layer 12 can range from about 80,500 to about 8,050,000 ohm meters.

In a specific embodiment of this invention, the cushioned layer 12 is a mixed-cell cellular material, available under the tradename "R4533T", from Rubatex Corporation of Bedford, Va. This material is a blend of butyl rubber and ethylene propylene diene monomers having the following specifications: a compression deflection of 3 to 7 pounds per square inch, a density of 9 to 12 pounds per cubic foot, a compression set of about 7 percent, and a thickness of about 0.12 inches. The cushioned layer 12 contains particles of carbon black, which is available as product XC-72 from the Cabot Corporation of Boston, Mass., substantially homogeneously distributed throughout the layer.

The woven fabric 14, which is bonded to the cushioned layer 12, is constructed from about 90 percent to about 99 percent by weight of man-made or synthetic noncellulosic fibers 20. The noncellulosic fibers 20 are beneficial in transporting moisture away from the wearer's foot and into the cushioned layer 12 and also resist degradation from human perspiration. The fibers 20 should range from about 1 to about 24 denier in size, preferably, from about 1 to about 7 denier in size. The fibers 20 should have a dry breaking tenacity ranging from about 1.2 to about 9.5 grams per denier, preferably, from about 2.4 to about 5.5 grams per denier. The fibers 20 should also be absorbent. When the fibers 20 are measured using "moisture regain", which is expressed as a percentage of the moisture-free weight at 70 degrees F. and at 65 percent relative humidity, the fibers 20 should have an absorbency in the range of about 0.0 to about 6.0 percent, preferably, from about 0.4 to about 0.8 percent.

The noncellulosic fibers 20 can be selected from the group consisting of acetate, acrylic, aramid, glass, modacrylic olefin, polyester, rayon and spandex fibers. To enhance their performance, the fibers 20 can be treated with a hydrophobic surfactant material to increase the rate at which absorbed moisture can be dispersed over the volume of the fibers 20. This treatment effectively transports moisture to the edge, or untreated areas, of the upper layer of the woven fabric 14 so that evaporation can be hastened. This process can be envisioned as a "reverse wicking" phenomena by the treated fibers of the woven fabric 14. The surfactant can be applied to the fabric 14 by spraying or by immersion coating and is then allowed to dry. The surfactant may be either zone coated or applied in a continuous manner across the width of the fabric 14. It should be realized that the noncellulosic fibers 20 can also be treated with a hydrophilic surfactant to decrease the rate at which absorbed moisture can be dispersed over the volume of the noncellulosic fibers 20, if this is desired. A specific hydrophilic surfactant used is Triton ® X-102 currently marketed by Union Carbide Chemicals and Plastics Company, Inc.

The woven fabric 14 contains from about 1 percent to about 10 percent by weight of noncorrosive, electrically conductive elements or fibers 22. These noncorrosive, electrically conductive fibers 22 should be continuous strands which facilitate transfer of the electrical charges from the wearer's foot down into the cushioned layer 12. The continuous fibers 22 can be interwoven into the woven fabric 14 in either the warp or the fill directions. Continuity is provided by the natural oscillations of the conductive fibers, at the minima position in the woven fabric 14, without the use or requirement of a binder material. This is an advantage over U.S. Pat. No. 4,926,570 issued to Fohst. Other ways of combining the noncorrosive, electrically conductive fibers 22 into the woven fabric 14 can also be utilized.

The noncorrosive, electrically conductive fibers 22 can include copper, aluminum, nickel, chromium, zinc, carbon, stainless steel, monel, duralumin, or other alloys of copper, aluminum, nickel, chromium, zinc or other type of nonoxidating metallic fibers. The noncorrosive, electrically conductive elements or fibers 22 should preferably be continuous fibers having a diameter from about 12 to about 250 micrometers, preferably, from about 12 to about 75 micrometers.

The woven fabric 14 should have a fabric count, expressed as the sum of the warp and fill numbers, of between about 25 to about 300, preferably, from about 55 to about 75.

By varying the amount of the noncorrosive, electrically conductive fibers 22 interwoven within the woven fabric 14, just about any value of "overall electrical resistance" can be obtained. Generally, the "overall electrical resistance" of the woven fabric 14 should range from about 1 to about 100 ohms.

In a specific embodiment of this invention, the fabric 14 is a plain weave fabric, available under the trade name "Special Combination—Blue", from Industrial Fabrics Corporation of Minneapolis, Minn. The fabric contains about 97 percent by weight of polyester fibers, and about 3 percent by weight of 304 stainless steel fibers. The polyester fibers have an average size of about 3 denier, a dry breaking tenacity of about 5.5 grams per denier; and an absorbency, measured as moisture regain expressed as a percentage of the moisture-free weight at 70 degrees F. and at 65 percent relative humidity, of about 0.8 percent. The fabric count, expressed as the sum of the warp and fill numbers, is 65 (39×26/inch). The stainless steel fibers, which are available as product "BK-50" from Bekaert Fibre Technologies of Zwevegem, Belgium, have an average diameter of about 75 micrometers.

The electrically nonconductive adhesive 16 bonds the woven fabric 14 to the cushioned layer 12. The nonconductive adhesive 16 will be inhibited from exuding through the woven fabric 14 while electrical charges may be conducted to the cushioned layer 12. One way this is accomplished is to use an electrically nonconductive adhesive 16 which is resistant to human perspiration. The electrically nonconductive adhesive 16 is applied so that some of the noncorrosive electrically conductive elements 22, in the fabric 14, are in contact (see point 24 in FIG. 2) with the cushioned layer 12. For example, the electrically nonconductive adhesive 16 may be applied in a thin layer to allow some of the noncorrosive, electrically conductive elements 22 to pass therethrough and provide a conductive path through the electrically nonconductive adhesive 16.

The use of a very thin layer of a two-component polyurethane adhesive 16, that is quite intractable when cured, can maintain the spacial arrangement of the woven fabric 14, especially at the contact points 24. This is important because it is accomplished without the use of an electrically conductive additive. Typically, electrically conductive adhesives exhibit a phenomenon known as "physical aging" wherein the overall resistivity of the adhesive increases as a function of service-life. This is due to small rearrangements of the molecules within the adhesive which in turn displace the conductive particles dispersed throughout the adhesive with respect to each other. As the conductive particles are displaced, the current composing electrons have more difficulty tunnelling between adjacent conductive particles. Our electrically nonconductive adhesive 16 is more stable toward the in-shoe environment than an electrically conductive particle-filled latex emulsion. Our electrically nonconductive adhesive 16 is also less likely to be subjected to physical aging on the molecular level. Until now, it has not been obvious, to those skilled in the shoe insole art, that the combination of an electrically nonconductive adhesive 16 and a woven fabric 14 containing electrically conductive fibers could produce a more stable shoe insole.

Generally, the electrically nonconductive adhesive 16 should have a volume resistivity of between about 80,500 to about 80,500,000 ohm meters. More preferably, the volume resistivity will range from about 8,050,000 to about 80,500,000 ohm meters. The adhesive 16 can be applied in a weight per unit area which ranges from about 0.05 to about 150 pounds per thousand square feet of joint area. More specifically, the adhesive 16 can be applied in a weight per unit area of from about 0.1 to about 15 pounds per thousand square feet of joint areas.

As to other properties, it is desirable that the electrically nonconductive adhesive 16 have a peel strength which ranges from about 12–500 pounds per inch, preferably, from about 50–75 pounds per inch.

The electrically nonconductive adhesive 16 can be a synthetic compound or a synthetic compound which is capable of being thermoset. Such a compound may contain the reaction products of polyfunctional isocyanates and polyhydroxy alcohols. More specifically, the nonconductive adhesive 16 can be a two-part polyol/-diisocyanate compound, i.e. polyurethane derived from polyols having a molecular weight from about 500 to about 3000.

In a specific embodiment of this invention, the electrically nonconductive adhesive 16 is a two-part polyol/-diisocyanate compound derived from polyols having a molecular weight ranging between about 500 to about 800.

Figure 3:
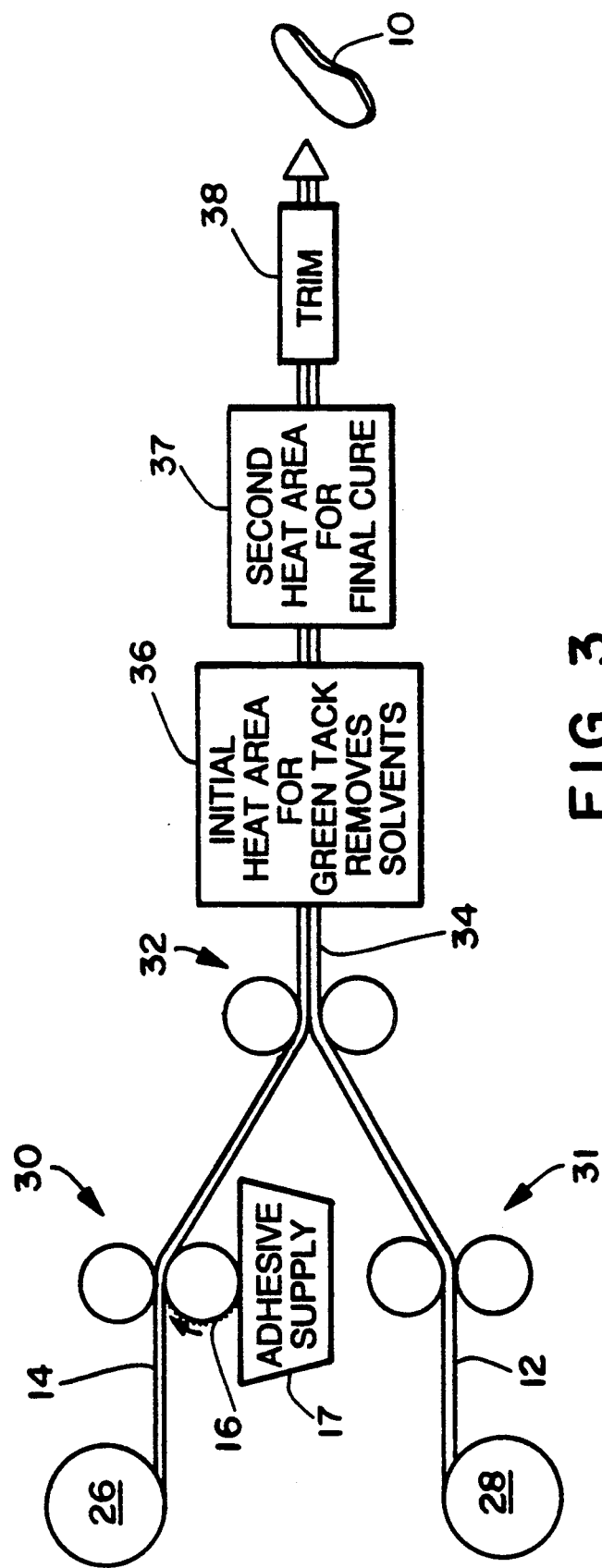
FIG. 3 is a schematic view of a process for making the electrically conductive shoe insole.

Referring to FIG. 3, a method for making the electrically conductive shoe insoles 10 is depicted. The method includes laminating or bonding the woven fabric 14 to an upper surface of the cushioned layer 12 with an electrically nonconductive adhesive 16. The first step entails providing a first supply roll 26 of woven fabric 14 in sheet form and a second supply roll 28 of cushioned layer 12 in sheet form. The electrically nonconductive adhesive 16, which is contained in a container 17, is then applied to one surface of the woven fabric 14 such as by a roll mechanism 30. The roll mechanism 30 can consist of two rotating rolls wherein the lower roll contacts the bath of adhesive 16 contained in the container 17 and transports the adhesive 16 onto the lower surface of the woven fabric 14. The adhesive could also be spread onto the woven fabric 14 by other means known to those skilled in the art.

The third step of the method involves laminating or bonding the woven fabric 14 to the cushioned layer 12 to form a laminated sheet 34. This can be accomplished by passing the cushioned layer 12 through the nip of a pair of guide rollers 31 and aligning the cushioned layer 12 with the woven fabric 14. The woven fabric 14 and the cushioned layer 12 are then passed through the nip of a roller mechanism 32. The roller mechanism 32 includes a pair of rotatable rolls aligned relative to one another so as to apply pressure to the material passing therebetween. This pressure will cause the adhesively-coated lower surface of the woven fabric 14 to bond to the upper surface of the cushioned layer 12.

The fourth step of the method involves curing the electrically nonconductive adhesive 16 by exposing the laminated sheet 34 to a source of heat. As depicted, the heat source consists of an initial heat area 36 wherein solvents are removed and a second heat area 37 where the laminate 34 is finally cured. The heat source can be an electric ceramic oven or other type of heater known to those skilled in the art. It should also be stated that the laminate 34 could be initially heated and finally cured all in one step if desired. The heating step should be carried out at a temperature of about 350 degrees Fahrenheit (°F.) for a period of approximately 15 minutes. It should be noted that the time and temperature can vary depending upon the thickness and composition of the laminated sheet 34, the type of heating apparatus used, etc. The laminated sheet 34 is then cooled to room temperature and should be maintained at room temperature for about 5 minutes.

The last step of the method involves forming the laminated sheet 34 into electrically conductive shoe insoles 10. This is accomplished by cutting the laminated sheet 34 into shoe insoles 10 with a die stamping press mechanism 38.

While the invention has been described in conjunction with a specific embodiment, it is to be understood that many alternatives, modifications, and variations will be apparent to those skilled in the art in light of the aforegoing description. Accordingly, this invention is intended to embrace all such alternatives, modifications and variations which fall within the spirit and scope of the appended claims.

I claim:

1. An electrically conductive shoe insole comprising:
   a) a foamed cushioned layer containing an electrically conductive material;
   b) a fabric positioned above said cushioned layer, said fabric containing noncellulose fibers and noncorrosive electrically conductive fibers; and
   c) electrically nonconductive adhesive means for bonding said fabric to said cushioned layer.

2. The shoe insole of claim 1 wherein said nonconductive adhesive means is applied to said fabric such that said noncorrosive, electrically conductive fibers contact said cushioned layer.

3. The shoe insole of claim 1 wherein said nonconductive adhesive means comprises a two-part polyol/diisocyanate compound.

4. The shoe insole of claim 1 wherein said cushioned layer is formed from at least one of the following materials: neoprene, butyl rubber, rubbers containing ethylene propylene diene monomers, polyvinyl chloride.

5. The shoe insole of claim 1 wherein said cushioned layer has carbon black particles distributed therein.

6. An electrically conductive shoe insole comprising:
   a) a cushioned layer containing an electrically conductive material;
   b) a woven fabric positioned above said cushioned layer, said fabric having from about 90 to 99 percent by weight of noncellulose fibers and from about 1 to 10 percent by weight of noncorrosive electrically conductive fibers, said noncorrosive, electrically conductive fibers being interwoven into said fabric, said noncellulose fibers being treated with a hydrophilic surfactant to decrease the rate at which absorbed moisture can be dispersed over the volume of said noncellulosic fibers; and
   c) electrically nonconductive adhesive means for bonding said woven fabric to said cushioned layer.

7. The shoe insole of claim 6 wherein said noncorrosive, electrically conductive fibers are made from at least one of the following materials: copper, aluminum, nickel, chromium, zinc, carbon, stainless steel, monel, duralumin, or other alloys of copper, aluminum, nickel, chromium, or zinc.

8. The shoe insole of claim 6 wherein said electrically nonconductive adhesive means is applied to said fabric such that said noncorrosive, electrically conductive fibers contact said cushioned layer.

9. The shoe insole of claim 6 wherein said electrically nonconductive adhesive means is thinly applied to said woven fabric to enable an electrical charge to be transferred from said noncorrosive, electrically conductive fibers to said cushioned layer.

10. The shoe insole of claim 6 wherein said noncellulosic fibers are selected from a group consisting of: acetate, acrylic, aramid, glass, modacrylic olefin, polyester, rayon, and spandex fibers.

11. An electrically conductive shoe insole for use in a shoe comprising:
   a) a foamed cushioned layer containing an electrically conductive material which can absorb shock, distribute pressure, and transfer electrical charges to said shoe;
   b) a woven fabric positioned cushioned layer, said fabric having from about 90-99% by weight of continuous noncellulose fibers and from about 1-10% by weight of continuous noncorrosive electrically conductive fibers, said fabric capable of transporting moisture away from a user's foot; and
   c) electrically nonconductive adhesive means for bonding said woven fabric to said cushioned layer, said adhesive permitting the transfer of electrical charges from said user's foot to said shoe.

12. The shoe insole of claim 11 wherein said noncorrosive electrically conductive fibers are made from at least one of the following materials: copper, aluminum, nickel, chromium, zinc, carbon, stainless steel, monel, duralumin, or other alloys of copper, aluminum, nickel, chromium, or zinc.

13. The shoe insole of claim 11 wherein said electrically nonconductive adhesive means is applied to said fabric such that said noncorrosive electrically conductive fibers contact said cushioned layer.

14. The shoe insole of claim 11 wherein said electrically nonconductive adhesive means is thinly applied to said fabric to enable an electrical charge to be transferred from said noncorrosive, electrically conductive fibers to said cushioned layer.

15. An electrically conductive shoe insole comprising:
   a) a foamed cushioned layer containing an electrically conductive material, said material made from butyl rubber and ethylene propylene diene monomers;
   b) a woven fabric positioned cushioned layer, said fabric having from about 90–99% by weight of polyester fibers and from about 1–10% by weight of nonoxidating metallic fibers interwoven therein, said polyester fibers being treated with a hydrophobic surfactant to increase the rate at which absorbed moisture can be dispersed over the volume of said noncellulose fibers; and
   c) electrically nonconductive adhesive means for bonding said fabric to said cushioned layer.

16. The shoe insole of claim 15 wherein said electrically nonconductive adhesive means comprises a two-part polyol/diisocyanate compound derived from polyols having a polyol molecular weight ranging from about 500–3000.

* * * * *

UNITED STATES PATENT AND TRADEMARK OFFICE
CERTIFICATE OF CORRECTION

PATENT NO. : 5,319,867
DATED : June 14, 1994
INVENTOR(S) : Fredric J. Weber

It is certified that error appears in the above-identified patent and that said Letters Patent is hereby corrected as shown below:

Column 8, line 53, after "positioned" insert --above said--.

Column 10, line 1, after "positioned" insert --above said--.

Column 10, line 8, change "noncellulose" to --noncellulosic--.

Signed and Sealed this

Thirty-first Day of January, 1995

Attest:

BRUCE LEHMAN

Attesting Officer

Commissioner of Patents and Trademarks